(12) United States Patent
Choi et al.

(10) Patent No.: US 9,328,115 B2
(45) Date of Patent: May 3, 2016

(54) PROCESS FOR PREPARING MEROPENEM TRIHYDRATE

(71) Applicant: DAEWOONG PHARMACEUTICAL CO., LTD., Seongnam-si, Gyeonggi-do (KR)

(72) Inventors: Soo-Jin Choi, Yongin-si (KR); Byung-Goo Lee, Suwon-si (KR); Hee-Kyoon Yoon, Cheongju-si (KR); Sung-Woo Park, Gwangju-si (KR); Sun-Ah Jun, Yongin-si (KR); Kyung-Ho Lee, Osan-si (KR); Byung-Jo Lim, Yongin-si (KR)

(73) Assignee: DAEWOONG PHARMACEUTICAL CO., LTD., Seongnam-si, Gyeonggi-do (KR)

( * ) Notice: Subject to any disclaimer, the term of this patent is extended or adjusted under 35 U.S.C. 154(b) by 0 days.

(21) Appl. No.: 14/655,875

(22) PCT Filed: Nov. 21, 2013

(86) PCT No.: PCT/KR2013/010594
§ 371 (c)(1),
(2) Date: Jun. 26, 2015

(87) PCT Pub. No.: WO2014/104583
PCT Pub. Date: Jul. 3, 2014

(65) Prior Publication Data
US 2015/0353554 A1 Dec. 10, 2015

(30) Foreign Application Priority Data
Dec. 28, 2012 (KR) .......................... 10-2012-0156100

(51) Int. Cl.
*C07D 477/06* (2006.01)
*C07D 477/20* (2006.01)
*C07D 487/04* (2006.01)

(52) U.S. Cl.
CPC ............ *C07D 477/06* (2013.01); *C07D 477/20* (2013.01); *C07D 487/04* (2013.01)

(58) Field of Classification Search
None
See application file for complete search history.

(56) References Cited

U.S. PATENT DOCUMENTS

| 4,888,344 | A | 12/1989 | Sunagawa et al. |
| 4,933,333 | A | 6/1990 | Sunagawa et al. |
| 4,943,569 | A | 7/1990 | Sunagawa |
| 5,122,604 | A | 6/1992 | Sunagawa et al. |
| 8,148,520 | B2 | 4/2012 | Surulichamy et al. |
| 2009/0264643 | A1 | 10/2009 | Surulichamy et al. |
| 2012/0065392 | A1 | 3/2012 | Song et al. |
| 2012/0095210 | A1 | 4/2012 | Surulichamy et al. |

FOREIGN PATENT DOCUMENTS

| KR | 10-1142757 B1 | 5/2012 |
| WO | 2011/141847 A1 | 11/2011 |

*Primary Examiner* — Golam M M Shameem
*Assistant Examiner* — Laura Daniel
(74) *Attorney, Agent, or Firm* — Vorys, Sater, Seymour & Pease LLP; Mih Suhn Koh (57) ABSTRACT

Provided is a process for the preparation of meropenem trihydrate in high purity and high yield, including using a dry methanol solvate of meropenem, which can remarkably reduce the amount of residual solvents in the resulting product, thereby obtain meropenem trihydrate in high purity.

16 Claims, 6 Drawing Sheets

PROCESS FOR PREPARING MEROPENEM TRIHYDRATE

TECHNICAL FIELD

The present invention relates to a process for the preparation of meropenem trihydrate, more specifically to a process for the preparation of meropenem trihydrate in high purity and high yield, through using a dry methanol solvate of meropenem.

BACKGROUND ART

Meropenem, one of the carbapenem antibiotics, has the following formula 1; and the chemical name thereof is (4R, 5S,6S)-3-((3S,5S)-5-(dimethylcarbamoyl)pyrrolidin-3-ylthio)-6-((R)-1-hydroxyeth yl)-4-methyl-7-oxo-1-azabicyclo[3.2.0]hept-2-ene-2-carboxylic acid. Meropenem is clinically used in a trihydrate form, i.e., meropenem trihydrate (meropenem.$3H_2O$).

<Formula 1>

U.S. Pat. No. 4,888,344 has disclosed a process for preparing a crystalline meropenem trihydrate, which comprises dissolving non-crystalline meropenem in water at 30° C., cooling the solution in a water bath (whereupon precipitation of a small amount of crystals), and adding acetone to the mixture to form a precipitate. As an improved process, WO 2007/031858 has disclosed a process for preparing meropenem trihydrate, which comprises dissolving meropenem or its hydrate in water in the presence of a base such as ammonia, optionally filtering through micron filter, adjusting the pH to 4.0 to 7.0 with an acid such as formic acid, and adding solvent (anti-solvent) to yield meropenem trihydrate. However, the process disclosed in U.S. Pat. No. 4,888,344 includes heating in the dissolving step, which causes forming degradation products, thereby resulting in unsatisfactory purity and low yield of the product, i.e., meropenem trihydrate. And also, the process disclosed in WO 2007/031858 includes additional steps for using a base and adjusting the pH with an acid, which makes the process complicated. In addition, the process disclosed in WO 2007/031858 may cause unwanted residual substances (for example, salts originated from acid-base reaction, fine dusts during the pH adjustment, metallic foreign substances, etc.) in the product.

In addition, WO 2011/141847 has disclosed a process for preparing meropenem trihydrate, which comprises dissolving non-sterile meropenem trihydrate in cold methanol to obtain a clear solution, optionally treating with carbon and/or filtering through micron filter, and adding an anti-solvent thereto. However, in order to obtain the clear solution in cold methanol, it is required to use excessive amounts of methanol. That is, in order to completely dissolve meropenem in cold (about 0° C.) methanol, it is required to use at least 8 times of methanol based on the weight of meropenem (for example, 80 ml of methanol based on 10 g of meropenem). If heating is carried out in order to avoid using the excessive amounts of methanol, degradation products of meropenem are formed, which results in lowering purity of the product. Moreover, the use of excessive amounts of methanol remarkably increases the amount of the anti-solvent used, which makes it difficult to apply the process to industrial mass production. Especially, the use of excessive amounts of both methanol and the anti-solvent causes a problem of high amounts of residual solvents in the product, i.e., meropenem trihydrate.

DISCLOSURE OF INVENTION

Technical Problem

The present inventors performed various researches for developing a process for preparing meropenem trihydrate, which can minimize forming degradation products and unwanted foreign substances, along with giving high yield. The present inventors found that the methanol solvate isolated as a solid form, which was obtained from conversion of meropenem or its hydrate (e.g., crude hydrates), showed remarkably increased water-solubility in comparison with meropenem or its hydrate; and therefore can be easily dissolved in water even at low temperature. And also, the present inventors found that the subsequent step for forming meropenem trihydrate through using an anti-solvent (after dissolving the dry methanol solvate of meropenem in water) could be performed at low temperature, which resulted in minimizing the formation of degradation products and unwanted foreign substances, thereby accom-plishing high purity (especially, low level of residual solvents) and high yield of the product.

Therefore, it is an object of the present invention to provide a process for the preparation of meropenem trihydrate through using a dry methanol solvate of meropenem.

It is another object of the present invention to provide the dry methanol solvate of meropenem.

Solution to Problem

In accordance with an aspect of the present invention, there is provided a process for preparing a trihydrate form of the compound of Formula 1, which comprises:

(a) dissolving a dry methanol solvate of the compound of Formula 1 (i.e., meropenem) in water to obtain a solution;

<Formula 1>

(b) adding an anti-solvent to the solution obtained from the step (a) to form a precipitate; and

(c) isolating the precipitate from the mixture obtained from the step (b).

Figure 1:
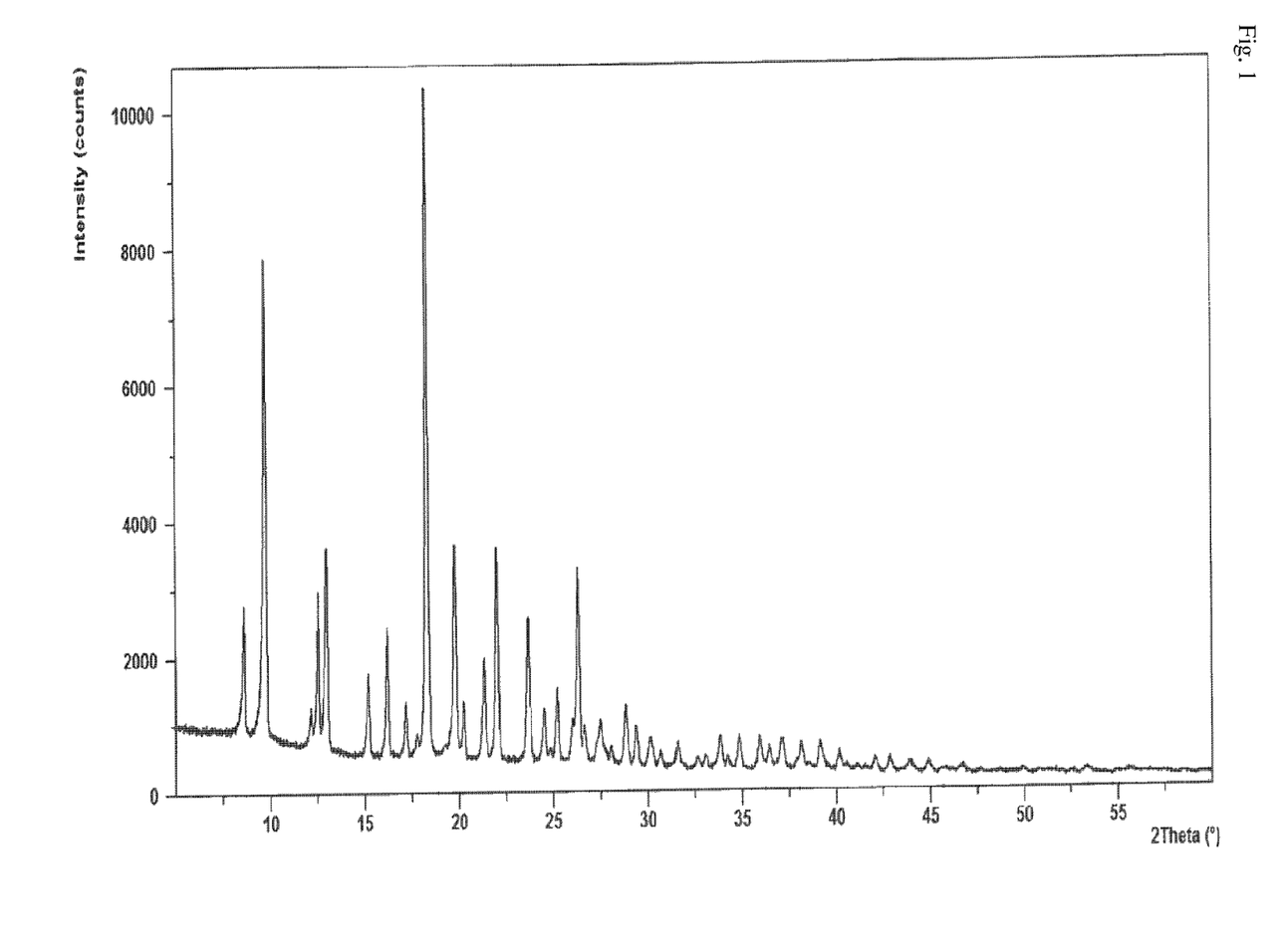
FIG. 1 shows the powder X-ray diffraction spectrum of the crystalline methanol solvate of meropenem obtained in Example 1.

In an embodiment of the present invention, the dry methanol solvate of meropenem may be a crystalline form having a powder X-ray diffraction spectrum comprising peaks at 8.62, 9.76, 12.17, 12.56, 12.99, 15.23, 16.20, 17.20, 18.33, 19.79, 20.24, 21.34, 22.03, 23.69, 24.54, 25.19, and 26.31

°2θ(±0.2°), specifically a crystalline form having the powder X-ray diffraction spectrum of FIG. 1.

The dry methanol solvate of meropenem may be obtained by a process comprising: (i) slurrying the compound of Formula 1 or its hydrate in methanol to form a methanol solvate thereof; and (ii) filtering the slurry obtained from the step (i), followed by drying the resulting methanol solvate.

In accordance with another aspect of the present invention, there is provided a methanol solvate of the compound of Formula 1:

<Formula 1>

Advantageous Effects of Invention

It is newly found by the present invention that the methanol solvate isolated as a solid form shows remarkably increased water-solubility in comparison with meropenem or its hydrate; and therefore can be easily dissolved in water even at low temperature (for example, −20° C. to 20° C.). And also, it is newly found by the present invention that the subsequent step for forming meropenem trihydrate through using an anti-solvent (after dissolving the dry methanol solvate of meropenem in water) could be performed at low temperature, i.e., at the temperature ranging from −20° C. to 20° C., preferably −10° C. to 5° C. Therefore, the process of the present invention can minimize forming degradation products and unwanted foreign substances and accomplish high yield, thereby being able to suitably apply to industrial mass production. Especially, the process according to the present invention makes it possible to prepare meropenem trihydrate in high purity, along with minimizing residual solvents.

BEST MODE FOR CARRYING OUT THE INVENTION

The present invention provides a process for the preparation of meropenem trihydrate using a dry methanol solvate of meropenem (i.e., a methanol solvate form of meropenem which is isolated as a solid form) as a starting material. That is, the present invention provides a process for preparing a trihydrate form of the compound of Formula 1 (i.e., meropenem.3H$_2$O), which comprises: (a) dissolving a dry methanol solvate of the compound of Formula 1 in water to obtain a solution; (b) adding an anti-solvent to the solution obtained from the step (a) to form a precipitate; and (c) isolating the precipitate from the mixture obtained from the step (b).

<Formula 1>

It is newly found by the present invention that the methanol solvate isolated as a solid form shows remarkably increased water-solubility in comparison with meropenem or its hydrate; and therefore can be easily dissolved in water even at low temperature (for example, −20° C. to 20° C.). And also, it is newly found by the present invention that the subsequent step for forming meropenem trihydrate through using an anti-solvent (after dissolving the dry methanol solvate of meropenem in water) could be performed at low temperature, i.e., at the temperature ranging from −20° C. to 20° C., preferably −10° C. to 5° C. Therefore, the process of the present invention can minimize forming degradation products and unwanted foreign substances and accomplish high yield.

Figure 6:
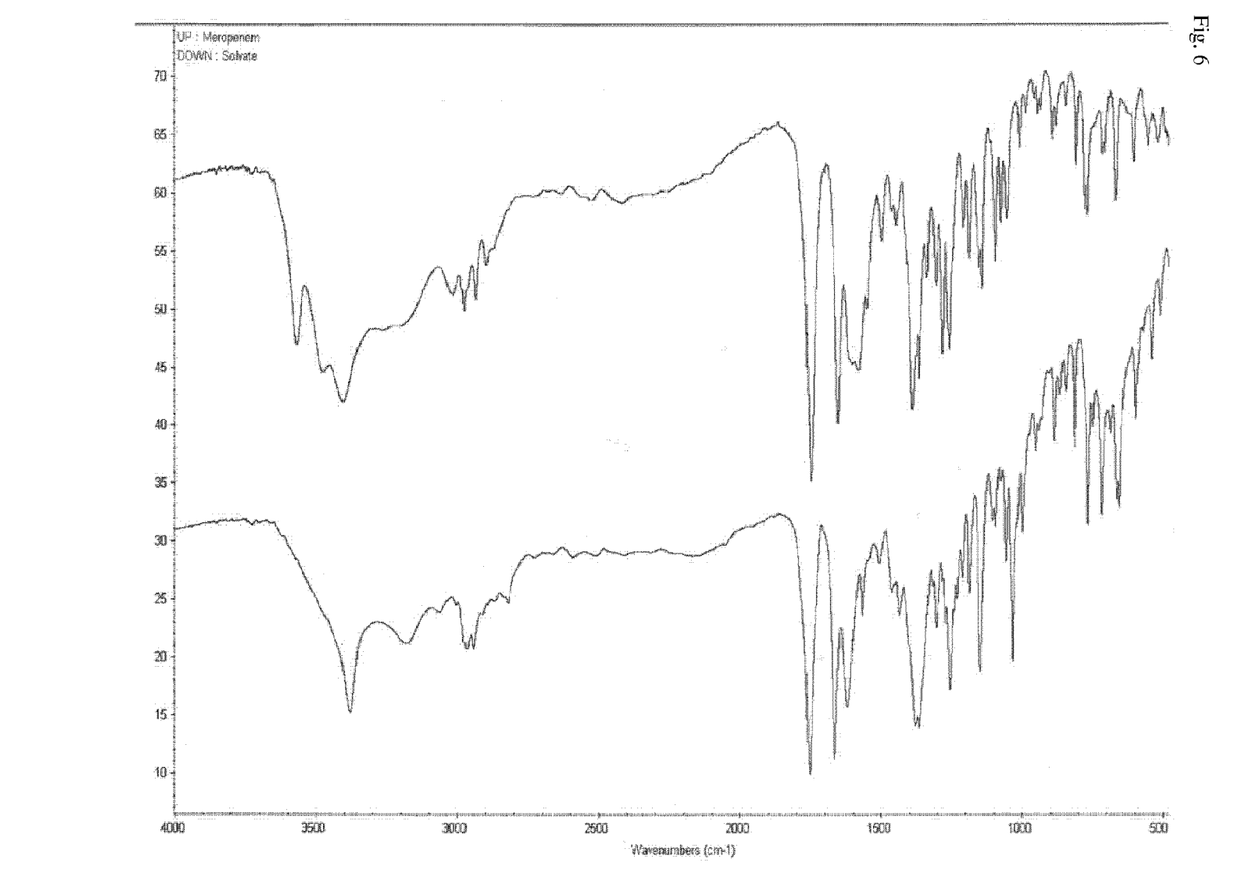
FIG. 6 shows the comparative Infrared (IR) spectrums of FIG. 4 and FIG. 5.

The dry methanol solvate of meropenem, which is used as a starting material in the process of the present invention, may be a crystalline form, preferably a crystalline form having a powder X-ray diffraction spectrum comprising peaks at 8.62, 9.76, 12.17, 12.56, 12.99, 15.23, 16.20, 17.20, 18.33, 19.79, 20.24, 21.34, 22.03, 23.69, 24.54, 25.19, and 26.31 °2θ(±0.2°). In an embodiment, the methanol solvate of meropenem is a crystalline form having the powder X-ray diffraction spectrum of FIG. 1. The methanol solvate of meropenem has characteristic peaks at 9.76 and 18.33 °2θ(±0.2°), in comparison with the powder X-ray diffraction spectrum of crystalline meropenem shown in FIG. 2. And also, as shown in FIG. 6, the methanol solvate of meropenem has an Infrared (IR) spectrum, which is different from that of non-solvate form of meropenem. Especially, the methanol solvate of meropenem has a characteristic peak at 1034 cm$^{-1}$, while the non-solvate form of meropenem does not have the peak thereof. In addition, there were differences between the methanol solvate of meropenem and the non-solvate form of meropenem, in the respective TGAs (thermogravimetric analyses), DSC (differential scanning calorimetries), and MPs (melting points). And also, as a result of analysis using the head space of gas chro-matography (under the analysis conditions of the following table 1), the contents of methanol in the dry methanol solvate of meropenem was 40,000 to 50,000 ppm (4 to 5%). And also, as a result of water-content analysis according to the Karl Fischer method, it was confirmed that the methanol solvate of meropenem had about 1% of water content. When the water content is calculated to molar ratio based on anhydrous meropenem, the methanol solvate of meropenem is a crystalline form having methanol in an equivalent ratio of 0.5 to 0.6.

The methanol solvate of meropenem may be prepared by a process comprising: (i) slurrying meropenem or its hydrate in methanol to form a methanol solvate thereof; and (ii) filtering the slurry obtained from the step (i), followed by drying the resulting methanol solvate.

The meropenem or its hydrate, which is used in the process for preparing the methanol solvate of meropenem as a starting material, may be obtained according to conventional methods. The meropenem may be a crystalline form and/or an amorphous form (e.g., amorphous meropenem prepared according to EP126587). The meropenem hydrate may be a hydrate form of crude meropenem (e.g., crude meropenem trihydrate) prepared according to WO 2010/104336. EP126587 and WO 2010/104336 are incorporated by reference in its entirety.

In the process for preparing the methanol solvate of meropenem, the slurrying (e.g., stirring in methanol) is performed preferably at low temperature, typically using cold methanol. For example, the slurrying may be performed preferably at −20° C. to 20° C., more preferably at −10° C. to 5° C. Methanol may be used in a ratio of 1 ml to 10 ml, preferably in a ratio of 2 ml to 6 ml, more preferably in a ratio of 3 ml to 4 ml, based on 1 g of meropenem or its hydrate; but not limited thereto. The slurrying may be performed typically for 1 minute to 3 hours. If necessary, the step (i) may further comprise seeding a methanol solvate of meropenem, so as to facilitate the formation thereof.

In the process for preparing meropenem trihydrate according to the present invention, the dissolving in the step (a) is performed preferably at low temperature, typically using cold water. For example, the dissolving may be performed preferably at 0° C. to 20° C., more preferably at 5° C. to 15° C. Water (for example, water for injection) may be used in a ratio of 10 ml to 50 ml, preferably in a ratio of 15 ml to 30 ml, based on 1 g of the methanol solvate of meropenem; but not limited thereto. Preferably, the resulting solution is subject to sterile filtration using a sterile filter. If necessary, after the solid obtained from the sterile filtration is washed with water (e.g., water for injection), the resulting washing solution is mixed with said solution (i.e., the solution obtained from the sterile filtration) and then the subsequent step is performed.

The anti-solvent used in the step (b) may be a solvent in which meropenem trihydrate is not soluble. For example, the anti-solvent used in the step (b) may be isopropyl alcohol, acetone, tetrahydrofuran, or ethanol, preferably isopropyl alcohol. The step (b) is also performed preferably at low temperature, typically using cold anti-solvent. For example, the step (b) may be performed preferably at −20° C. to 20° C., more preferably at −10° C. to 5° C., most preferably −5° C. to 5° C.

The step (b) may be repeated two or more times. If necessary, seeding meropenem trihydrate to the solution obtained from the step (a) may be further performed, prior to performing the step (b). Preferably, the step (b) may performed by ripening the resulting crystal through adding the anti-solvent repeatedly.

The resulting precipitate, i.e., the precipitate formed in the step (b), may be isolated according to conventional filtration and drying methods. If necessary, the isolated precipitate (i.e., meropenem trihydrate) may be washed with a cold (e.g., 0° C. to 5° C.) isopropyl alcohol solution. In an embodiment, the step (c) may be performed by filtering the mixture obtained from the step (b), washing the resulting solid with a mixed solvent of isopropyl alcohol and water (2:1, v/v), and then drying in vacuo at room temperature.

The present invention also provides the methanol solvate of meropenem, which is used as a starting material in the process for preparing meropenem trihydrate. That is, the present invention provides a methanol solvate of the compound of Formula 1:

<Formula 1>

The methanol solvate of the compound of Formula 1 may have a powder X-ray diffraction spectrum comprising peaks at 8.62, 9.76, 12.17, 12.56, 12.99, 15.23, 16.20, 17.20, 18.33, 19.79, 20.24, 21.34, 22.03, 23.69, 24.54, 25.19, and 26.31 °2θ(±0.2°). In an embodiment, the methanol solvate of the compound of Formula 1 is a crystalline form having the powder X-ray diffraction spectrum of FIG. 1. In another embodiment, the methanol solvate of the compound of Formula 1 has the Infrared (IR) spectrum of FIG. 4.

The present invention will be described in further detail with reference to the following examples. These examples are for illustrative purposes only and are not intended to limit the scope of the present invention.

EXAMPLE 1

Preparation and Evaluation of Methanol Solvate of Meropenem

To crude meropenem trihydrate (10 g, prepared according to WO 2010/104336), was added cold (0° C.) methanol (40 ml). The mixture was stirred for 2 hours, while the temperature thereof was maintaining at −5 to 0° C. After filtering the slurry, the resulting solid was dried in vacuo at room temperature to give methanol solvate of meropenem (9.8 g, 98.0%).

$^1$H NMR (CDCl$_3$, 400 MHz) δ 5.5 (1H), 5.20(2H), 4.75 (1H), 4.26 (2H), 3.4~3.8 (4H), 3.3 (2H), 3.0(6H), 2.62(1H), 1.2~1.3 (8H)

The water-solubilities of the methanol solvate of meropenem obtained in the above as well as meropenem trihydrate were measured at 26° C. As a result thereof, the methanol solvate of meropenem showed 57.6 mg/ml of water-solubility, while meropenem trihydrate showed 16.4 mg/ml of water-solubility.

Figure 2:
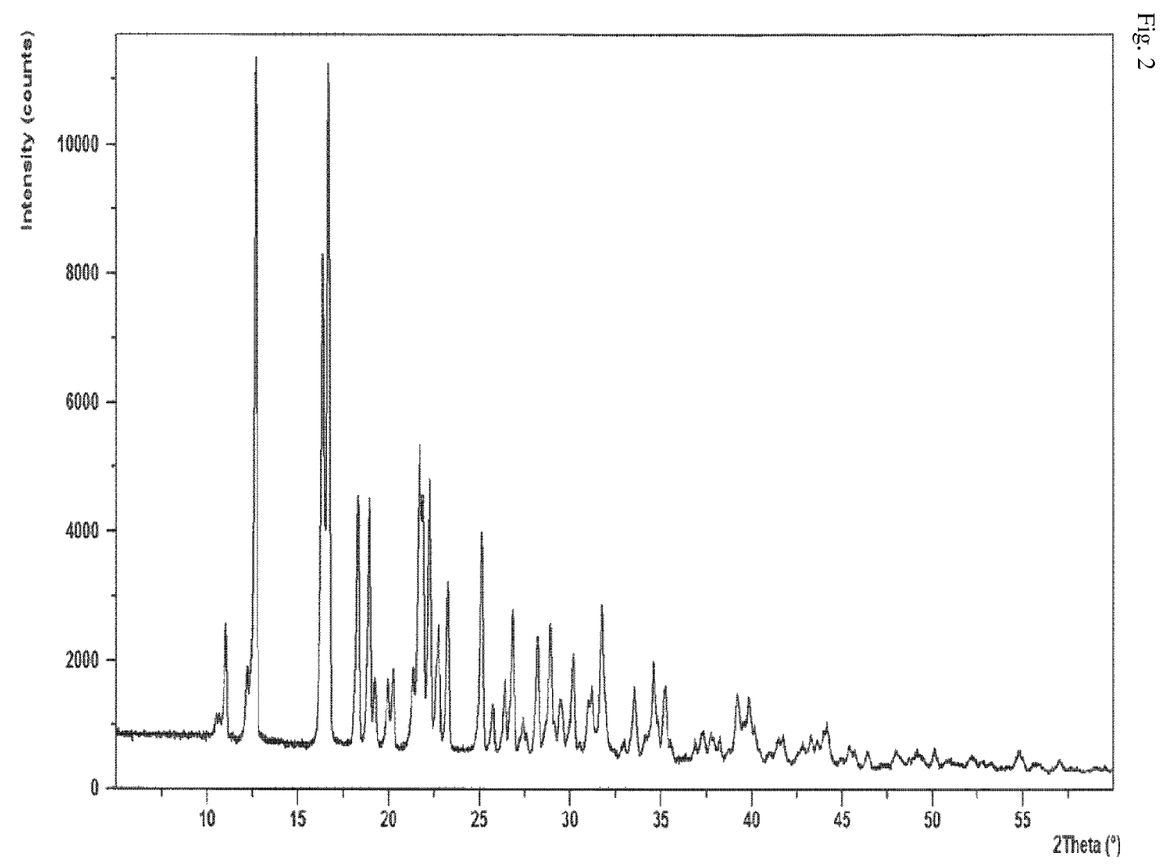
FIG. 2 shows the powder X-ray diffraction spectrum of crystalline meropenem.
Figure 3:
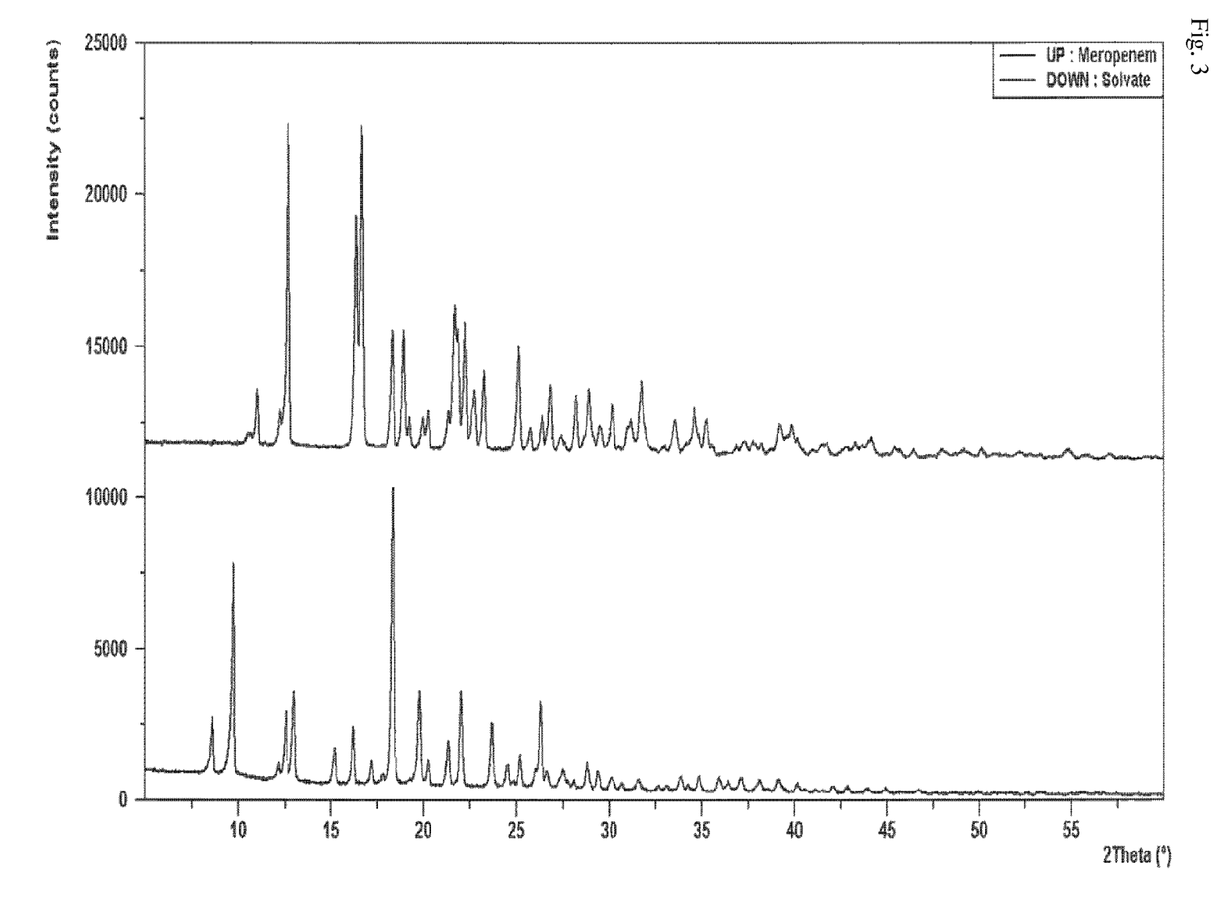
FIG. 3 shows the comparative powder X-ray diffraction spectrums of FIG. 1 and FIG. 2.

The methanol solvate of meropenem obtained in the above was a crystalline form and showed the powder X-ray diffraction spectrum of FIG. 1, which was measured with a X-ray diffractometer (model: Empyrean, Panalytical Co.) using Cu K alpha radiation source, under the conditions of an accelerating potential of 40 kV and a filament emission of 30 mA. For comparison, the powder X-ray diffraction spectrum of crystalline meropenem (which was measured according to the same method and conditions in the above) is shown in FIG. 2. And also, the comparative powder X-ray diffraction spectrums of FIG. 1 and FIG. 2 are shown in FIG. 3.

Figure 4:
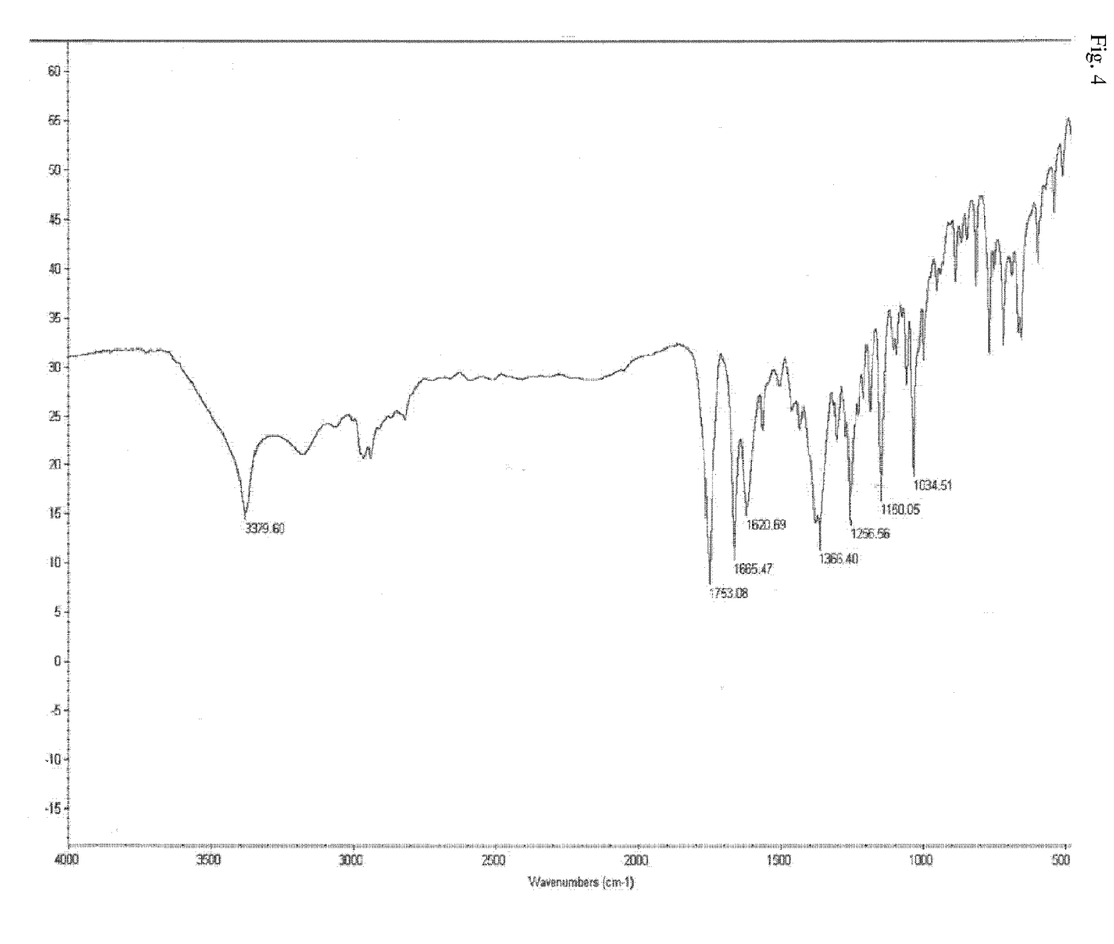
FIG. 4 shows the Infrared (IR) spectrum of the crystalline methanol solvate of meropenem obtained in Example 1.
Figure 5:
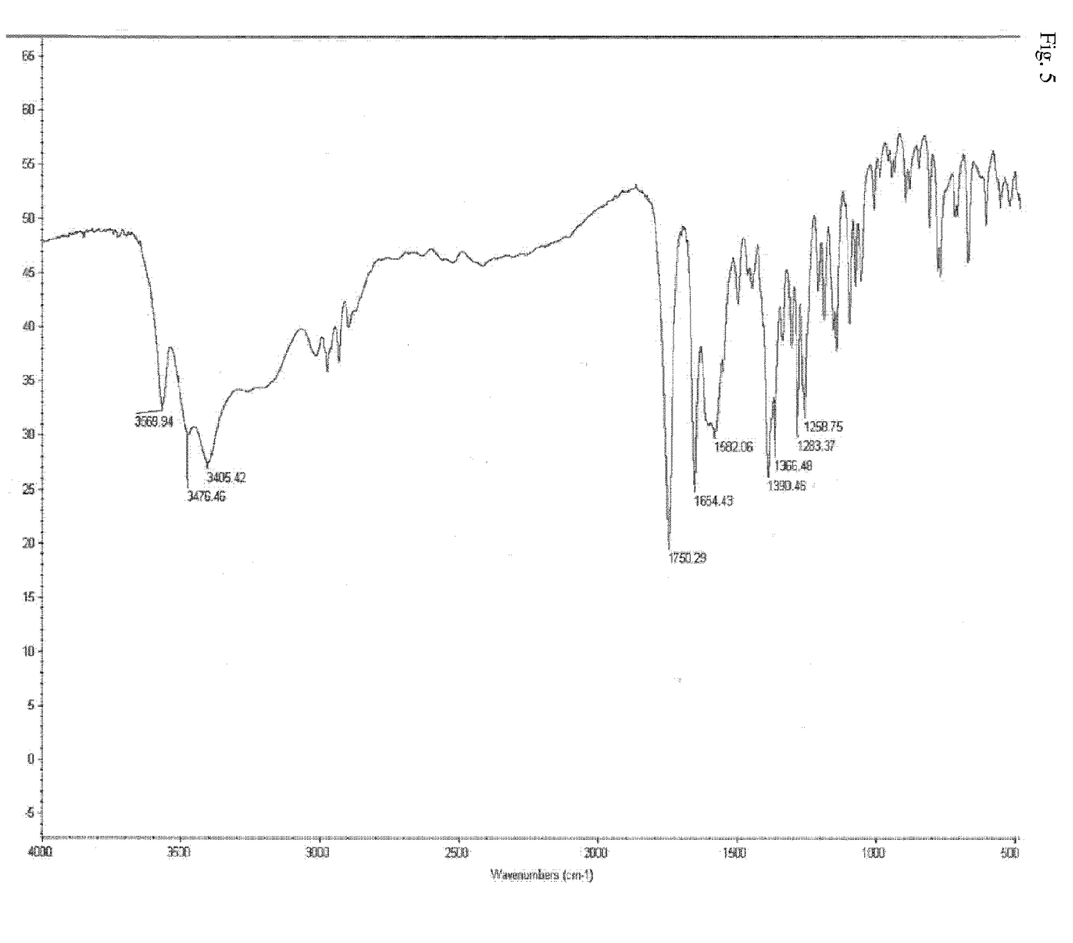
FIG. 5 shows the Infrared (IR) spectrum of crystalline meropenem.

In addition, the methanol solvate of meropenem obtained in the above showed the Infrared (IR) spectrum of FIG. 4, which was measured with an IR spectrometer (model: IS 10, Thermofisher Scientific Co.) using Mid-infrared Ever-Glo source, using a KBr pellet. For comparison, the Infrared (IR) spectrum of crystalline meropenem (which was measured according to the same method and conditions in the above) is shown in FIG. 5. And also, the comparative powder Infrared (IR) spectrums of FIG. 4 and FIG. 5 are shown in FIG. 6.

EXAMPLE 2

Preparation and Evaluation of Methanol Solvate of Meropenem

To crude meropenem trihydrate (10 g, prepared according to WO 2010/104336), was added cold (0° C.) methanol (40 ml). Seed (methanol solvate of meropenem, 1 g) was added to the mixture, which was stirred for 1 hour while the temperature thereof was maintaining at −5 to 0° C. After filtering the slurry, the resulting solid was dried in vacuo at room temperature to give methanol solvate of meropenem (9.8 g, 98.0%). The amount produced (and the yield) is the amount obtained by deducting the amount of the seed.

EXAMPLE 3

Preparation of Meropenem Trihydrate

Cold (10° C.) water for injection (180 ml) was added to the dry methanol solvate of meropenem (9.8 g) prepared in Example 1 or 2. The mixture was stirred for 2 minutes to obtain a solution (i.e., solution A which contains a small amount of undissolved solid), which was then filtered with a sterile filter (Sartorius, 5182507T1-LG). The isolated small amount of undissolved solid was washed with water for injection (20 ml). The resulting washing solution was mixed with the solution A and then cooled to below 10° C. Seed (meropenem trihydrate, 0.3 g) was added to the solution, which was then stirred at 0 to 5° C. for 1 hour. Cold (0° C.) isopropyl alcohol (30 ml) was added to the mixture, which was then stirred for 1 hour so as to ripen the crystal. Cold (0° C.) isopropyl alcohol (20 ml) was further added to the mixture, which was then stirred for 1 hour so as to ripen the crystal. Cold (0° C.) isopropyl alcohol (250 ml) was further added to the mixture, which was then stirred for 1 hour so as to ripen the crystal. And also, cold (0° C.) isopropyl alcohol (300 ml) was further added to the mixture, which was then stirred for 2 hours so as to ripen the crystal. After filtering the mixture, the resulting solid was washed with a mixed solvent (29.4 ml) of isopropyl alcohol and water (2:1, v/v), and then dried in vacuo at room temperature to give meropenem trihydrate (9.3 g, 94.9%). (HPLC purity: ≥99%)

$^1$H NMR (CDCl$_3$, 400 MHz) δ 5.5 (1H), 5.20(2H), 4.75 (1H), 4.26 (2H), 3.4~3.8 (4H), 3.3 (2H), 3.0(6H), 2.62 (1H), 1.2~1.3 (8H)

EXAMPLE 4

Preparation of Meropenem Trihydrate

Cold (10° C.) water for injection (180 ml) was added to the dry methanol solvate of meropenem (9.8 g) prepared in Example 1 or 2. The mixture was stirred for 2 minutes to obtain a solution (i.e., solution A which contains a small amount of undissolved solid), which was then filtered with a sterile filter (Sartorius, 5182507T1-LG). The isolated small amount of undissolved solid was washed with water for injection (20 ml). The resulting washing solution was mixed with the solution A and then cooled to below 10° C. Seed (meropenem trihydrate, 0.3 g) was added to the solution, which was then stirred at 0 to 5° C. for 1 hour. Cold (0° C.) acetone (30 ml) was added to the mixture, which was then stirred for 1 hour so as to ripen the crystal. Cold (0° C.) acetone (20 ml) was further added to the mixture, which was then stirred for 1 hour so as to ripen the crystal. Cold (0° C.) acetone (250 ml) was further added to the mixture, which was then stirred for 1 hour so as to ripen the crystal. And also, cold (0° C.) acetone (300 ml) was further added to the mixture, which was then stirred for 2 hours so as to ripen the crystal. After filtering the mixture, the resulting solid was washed with a mixed solvent (29.4 ml) of acetone and water (2:1, v/v), and then dried in vacuo at room temperature to give meropenem trihydrate (9.2 g, 94.5%). (HPLC purity: ≥99%)

$^1$H NMR (CDCl$_3$, 400 MHz) δ 5.5 (1H), 5.20(2H), 4.75 (1H), 4.26 (2H), 3.4~3.8 (4H), 3.3 (2H), 3.0(6H), 2.62 (1H), 1.2~1.3 (8H)

COMPARATIVE EXAMPLE 1

Preparation of Meropenem Trihydrate

Crude meropenem trihydrate (10.0 g) was completely dissolved in cold (0° C.) methanol (80 ml). To the resulting solution, were added EDTA (50 mg), Na$_2$S$_2$O$_4$ (100 mg), and ENO carbon (500 mg). The mixture was filtered to separate the carbon, which was then washed with cold (0° C.) methanol (5 ml). The washing solution was mixed with the filtrate and the resulting solution was filtered with a 0.2 μm filter (Sartorius, 5182507T1-LG). The resulting filtrate was cooled to 10° C. to 13° C. and then H$_2$O (135 ml) was added thereto. Acetone (600 ml) was added to the mixture, which was then stirred for 2 hours so as to ripen the crystal. After filtering the mixture, the resulting crystal was washed with a mixed solvent (40.0 ml) of acetone and water (3:1, v/v), and then dried to give meropenem trihydrate (8.9 g, 89.0%). (HPLC purity:≥ 99%)

COMPARATIVE EXAMPLE 2

Preparation of Meropenem Trihydrate

Crude meropenem trihydrate (10.0 g) was completely dissolved in cold (0° C.) methanol (80 ml). To the resulting solution, were added EDTA (50 mg), Na$_2$S$_2$O$_4$ (100 mg), and ENO carbon (500 mg). The mixture was filtered to separate the carbon, which was then washed with cold (0° C.) methanol (5 ml). The washing solution was mixed with the filtrate and the resulting solution was filtered with a 0.2 μm filter (Sartorius, 5182507T1-LG). The resulting filtrate was cooled to 10° C. to 13° C. and then H$_2$O (135 ml) was added thereto. Isopropyl alcohol (600 ml) was added to the mixture, which was then stirred for 2 hours so as to ripen the crystal. After filtering the mixture, the resulting crystal was washed with a mixed solvent (40.0 ml) of isopropyl alcohol and water (3:1, v/v), and then dried to give meropenem trihydrate (8.95 g, 89.5%). (HPLC purity: ≥99%)

EXPERIMENTAL EXAMPLE

Analysis of Residual Solvents

The residual solvents in each meropenem trihydrate prepared in Examples 3 and 4 and Comparative Examples 1 and 2 were analyzed using the head space of gas chro-matography under the conditions of the following table 1. The results thereof are shown in the following table 2.

TABLE 1

| | |
|---|---|
| Column | DB 624 (30 m * 0.52 mm) 3 micron film layer |
| Carrier gas | Helium |
| Flow rate | 3 ml/min |
| Injector temp. | 200° C. |
| Detector temp. | 240° C. |
| Oven temp. | Maintaining the initial temperature (40° C.) for 4 min. Elevating to 100° C. at 10° C./min and then maintaining for 2 min Elevating to 230° C. at 60° C./min and then maintaining for 3 min Cooling to 40° C. at 100° C./min and then maintaining for 1 min |
| Injector vol. | 1 ml |
| Heating (of head space) | 90° C. for 20 min. |
| Ratio | 7/1 |

TABLE 2

| | Residual solvent (ppm) | | |
|---|---|---|---|
| | Methanol | Acetone | Isopropyl alcohol |
| Example 3 | 87 | — | 405 |
| Example 4 | 289 | 226 | — |
| Comparative Example 1 | 2546 | 292 | — |
| Comparative Example 2 | 2561 | — | 2634 |

As shown in Table 2, the trihydrate forms of meropenem prepared according to the present invention showed remarkably lower levels of residual solvents, than those prepared according to the conventional methods.

The invention claimed is:

1. A process for preparing a trihydrate form of the compound of Formula 1, which comprises:
   (a) dissolving a dry methanol solvate of the compound of Formula 1 in a crystalline form having a power X-ray diffraction spectrum comprising peaks at 8.62, 9.76, 12.17, 12.56, 12.99, 15.23, 16.20, 17.20, 18.33, 19.79, 20.24, 21.34, 22.03, 23.69, 24.54, 25.19, and 26.31 °2θ (±0.2°) in water to obtain a solution;

<Formula 1>

(b) adding an anti-solvent to the solution obtained from step (a) to form a precipitate; and
   (c) isolating the precipitate from the mixture obtained from step (b).

2. The process according to claim 1, wherein the dry methanol solvate of the compound of Formula 1 is a crystalline form having the powder X-ray diffraction spectrum of FIG. 1.

3. The process according to claim 1, wherein the dry methanol solvate of the compound of Formula 1 is obtained by a process comprising:
   (i) slurrying the compound of Formula 1 or its hydrate in methanol to form a methanol solvate thereof; and
   (ii) filtering the slurry obtained from the step (i), followed by drying the resulting methanol solvate.

4. The process according to claim 3, wherein the slurrying is performed at −20° C. to 20° C.

5. The process according to claim 3, wherein the methanol is used in a ratio of 1 ml to 10 ml based on 1 g of the compound of Formula 1 or its hydrate.

6. The process according to claim 1, wherein the dissolving in the step (a) is performed at 0° C. to 20° C.

7. The process according to claim 6, wherein the dissolving in the step (a) is performed at 5° C. to 15° C.

8. The process according to claim 1, further comprising seeding meropenem trihydrate to the solution obtained from the step (a), prior to performing the step (b).

9. The process according to claim 1, wherein the anti-solvent in the step (b) is isopropyl alcohol, acetone, tetrahydrofuran, or ethanol.

10. The process according to claim 9, wherein the anti-solvent in the step (b) is isopropyl alcohol.

11. The process according to claim 1, wherein the step (b) is performed at −20° C. to 20° C.

12. The process according to claim 11, wherein the step (b) is performed at −10° C. to 5° C.

13. The process according to claim 1, wherein the step (b) is repeated two or more times.

14. A methanol solvate of the compound of Formula 1 in a crystalline form having a powder X-ray diffraction spectrum comprising peak at 8.62, 9.76, 12.17, 12.56, 12.99, 15.23, 16.20, 17.20, 18.33, 19.79, 20.24, 21.34, 22.03, 23.69, 24.54, 25.19, and 26.31 °2θ (±0.2°):

<Formula 1>

15. The methanol solvate of the compound of Formula 1 according to claim 14, which is a crystalline form having the powder X-ray diffraction spectrum of FIG. 1.

16. The methanol solvate of the compound of Formula 1 according to claim 14, having the Infrared spectrum of FIG. 4.

* * * * *